(12) United States Patent
Lyle

(10) Patent No.: US 8,308,818 B2
(45) Date of Patent: Nov. 13, 2012

(54) ADAPTIVE SPORTS ANKLE JOINT PROSTHESIS

(76) Inventor: David Kevin Lyle, The Woodlands, TX (US)

( * ) Notice: Subject to any disclaimer, the term of this patent is extended or adjusted under 35 U.S.C. 154(b) by 193 days.

(21) Appl. No.: 12/925,233

(22) Filed: Oct. 18, 2010

(65) Prior Publication Data
US 2012/0095572 A1   Apr. 19, 2012

(51) Int. Cl.
A61F 2/62   (2006.01)
A61F 2/66   (2006.01)

(52) U.S. Cl. ............................................ 623/38; 623/47

(58) Field of Classification Search ................... 623/38, 623/47, 52, 50
See application file for complete search history.

(56) References Cited

FOREIGN PATENT DOCUMENTS
JP   2004-166811 A  *  6/2004
* cited by examiner

*Primary Examiner* — David H. Willse

(57) ABSTRACT

An ankle joint prosthesis comprised of a central core element capable of attachment to an artificial leg, coupled to two side elements capable for attachment to an artificial foot. The medial and lateral side elements envelop the central core element lower region along a common central axis, and are coupled together by a mechanical fastening mechanism and can be rotated relative to the central core element and positively constrained to align in various orientations dependent of a specific grooved profile within each side element pair. The ankle joint orientation is affected by engaging an anterior and/or posterior located mechanical linkage enacting an upward linear movement on a guide pin plunger, thus allowing the side elements to rotate by a torque force from a torsion spring until reaching orientation held in place along a grooved profile. The load bearing elements shall be precision machined from Grade 5 Titanium.

4 Claims, 9 Drawing Sheets

ADAPTIVE SPORTS ANKLE JOINT PROSTHESIS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

The invention generally relates to an ankle joint prosthesis that can be positioned for walking, and effectively transitioned to multiple orientations as for use while engaging adaptive sports activities, and in regards to this invention; aquatic and equestrian activity.

The following patents may be relevant to the present invention:
U.S. PATENT DOCUMENTS
U.S. Pat. No. 911,243 February 1909 Johannesen
U.S. Pat. No. 2,749,557 June 1956 Riddle
U.S. Pat. No. 3,419,227 December 1968 Werkmeister et al.
U.S. Pat. No. 3,480,972 December 1969 Prahl
U.S. Pat. No. 4,413,360 November 1983 Lamb et al.
U.S. Pat. No. 4,865,611 September 1989 Al-Turaiki
U.S. Pat. No. 5,156,630 October 1992 Rappoport et al.
FOREIGN PATENT DOCUMENTS
0262319 January 1970 Russian Federation
2110806 October 1971 Federal Republic of Germany
0381347 May 1973 Russian Federation
1509641 May 1978 United Kingdom
0016268 October 1980 European Patent Office The most relevant patent to the present invention may be U.S. Pat. No. 5,156,630; Inventors: A. Rappoport, S. Shawe, and M. Ross; Issue Date 20 Oct. 1992. U.S. Pat. No. 5,156,630 to Rappoport, Shawe, & Ross is directed to an ankle joint prosthesis comprised of an upper part for attachment to an artificial leg and a lower part for attachment to an artificial foot, with the upper and lower parts rotatively coupled and capable of being fixed in a first position for walking, a second fixed position for swimming, or a free-flexing mode for rowing, and skiing.

Changing positions is effected by manually rotating a D-ring on the medial side of the ankle prosthesis by hand.

Materials of construction of the ankle body is precision machined from lightweight/high strength plastic.

Although the ankle joint prosthesis discussed above can be adjusted manually, it suffers some notable deficiencies, specifically; method of manipulation, limited fixed positions, and strength of materials utilized.

Manually rotating the ankle by hand requires the prosthesis wearer to be stationary by means of standing on one leg or sitting to be able to fix the ankle into and out of the locked positions; this is not a desirable transition mode if you desire to be dynamic into and out of the water, either at a beach, pool or climbing a boat ladder.

The fixed and locked positions are set for walking, and at approximately 75 degrees plantar flexion orientation for swim position only. The free-flex mode is used when the ankle joint is required to rotation freely, i.e. no resistance or ability to fix position.

The ankle embodiment is made from lightweight/high strength plastic, but may not be durable during high energy activity.

BRIEF SUMMARY OF THE INVENTION

A determined focus was concentrated on the deficiencies of the previously known ankle joint prosthesis. The applicant has invented an ankle joint prosthesis comprised of a central core element capable of attachment to an artificial leg, coupled with two side elements capable for attachment to an artificial foot. The medial and lateral side elements envelop the central core lower region along a common central axis, and are coupled together by means of mechanical fastening and can be rotated relative to the central core and positively constrained to align in various orientations dependent of a specific grooved profile within each side element pair. The ankle joint orientation is affected by engaging an anterior/posterior located mechanical linkage enacting an upward linear movement on a guide pin plunger, thus allowing the side elements to rotate by means of an imposed torque load reaching an intended orientation positively constrained within a grooved profile. The load bearing elements shall be precision machined from Grade 5 Titanium material. Mechanical linkages, fasteners, and springs shall be made from Series 300 Stainless Steel material. All materials shall be surface treated by a chemical passivation process enabling maximum corrosion resistance for use in salt water.

It is an object of the present invention to provide an ankle joint prosthesis which is a prosthetic adaptive sports ankle that can function with one central core and multiple interchangeable medial and lateral side elements, each pair unique of grooved profiles for various sports applications.

It is an object of the present invention to provide an ankle joint prosthesis that has a pair of unique mechanical linkages, which when engaged translates a linear motion directing a guide pin on a grooved profile allowing the medial and lateral side elements to rotate to an orientation held in place by spring and mechanical constraint.

It is an object of the present invention to provide an ankle joint prosthesis that has a unique mechanical linkage centrally located in the anterior and posterior of the central core so that the ankle joint prosthesis is applicable for either the lateral or medial side foot use without modification.

It is an object of the present invention to provide an ankle joint prosthesis that has unique grooved profile designs for specific sports that will allow the user to transition throughout the ankle's required range of motion when engaged in aquatic or equestrian activity.

It is an object of the present invention to provide an ankle joint prosthesis which is made of water proof and corrosion resistant materials, and is capable of withstanding the impact and moment forces of dynamic occurrences, thus shall be precision machined and fabricated from Grade 5 Titanium and Series 300 Stainless Steel material.

It is an object of the present invention to provide an ankle joint prosthesis which allows the user during aquatic activity to easily transition (from a terrestrial bipedal locomotion orientation to a plantar flexion orientation, and return to a terrestrial bipedal locomotion orientation) to and from the water without having to become stationary and manually rotate and lock the ankle into position by hand, which enables the water sports enthusiast improved confidence and safety during ingress and egress at the aquatic and terrestrial boundary.

It is an object of the present invention to provide an ankle joint prosthesis which allows the user during equestrian activity to easily transition (from a terrestrial bipedal locomotion orientation to a dorsal flexion orientation, and return to a terrestrial bipedal locomotion orientation) when in the saddle seat and stirrup without having to manually rotate and fix the ankle into the desired orientation by hand, which enables the equestrian enthusiast proper weight distribution providing improved balance and stability.

It is an object of the present invention to provide an ankle joint prosthesis which is compatible with prosthetic industry standard attachment components for attachment to an artificial leg and an artificial foot.

It is an object of the present invention to provide an ankle joint prosthesis for which one size fits all users, and is applicable for lateral or medial side leg/foot use without modification to the affecting mechanical linkage's location.

DETAILED DESCRIPTION OF THE INVENTION

Figure 1:
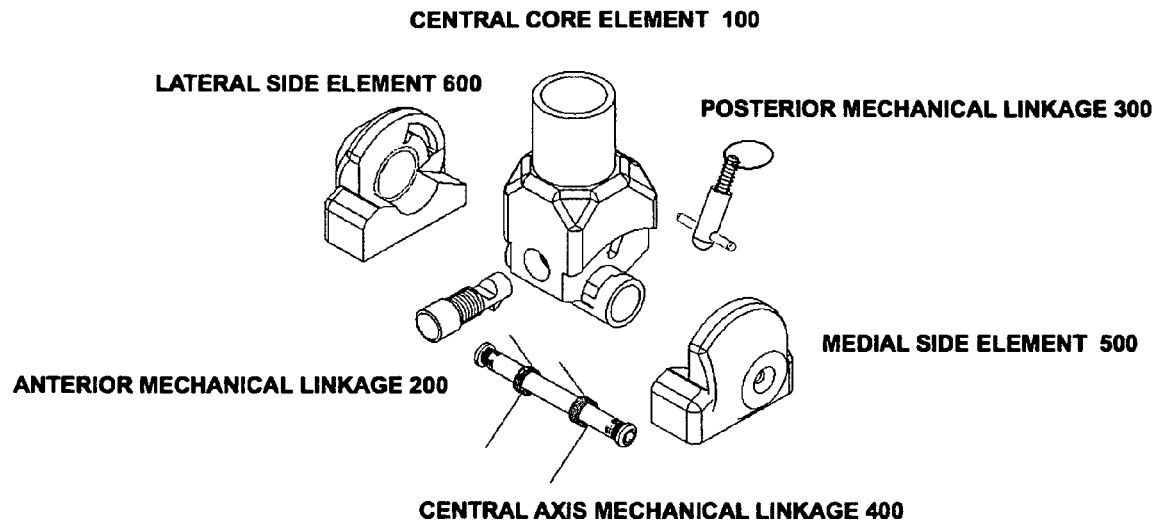
FIG. 1 Perspective Exploded View, Ankle Joint Prosthesis

Referring to FIG. 1, which illustrates an exploded perspective view of the embodiment of the present ankle joint prosthesis. The ankle joint embodiment generally is comprised of six key components; a central core element 100, an anterior mechanical linkage 200, a posterior mechanical linkage 300, a central axis mechanical linkage 400, a medial side element 500, and a lateral side element 600.

Figure 2:
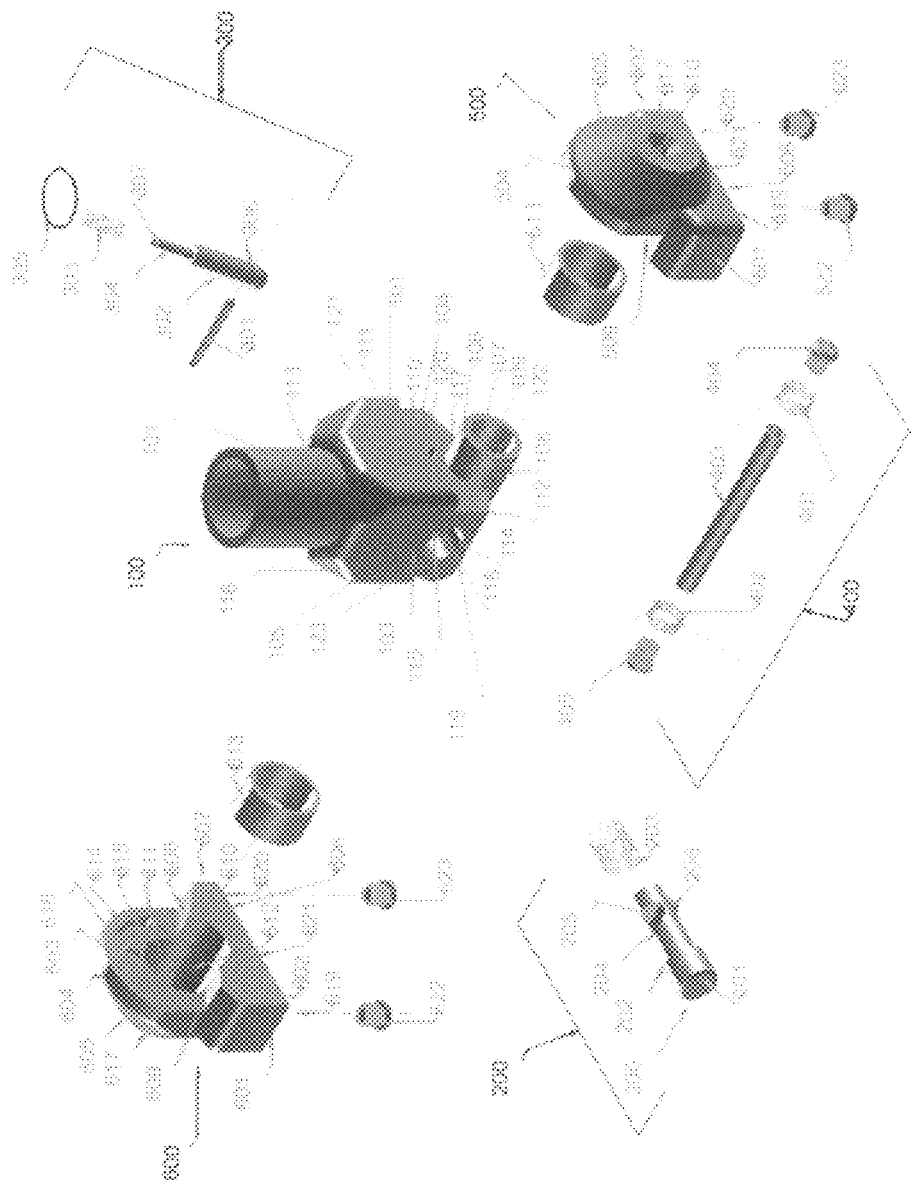
FIG. 2 Detailed Parts Exploded View, Ankle Joint Prosthesis
Figure 3:
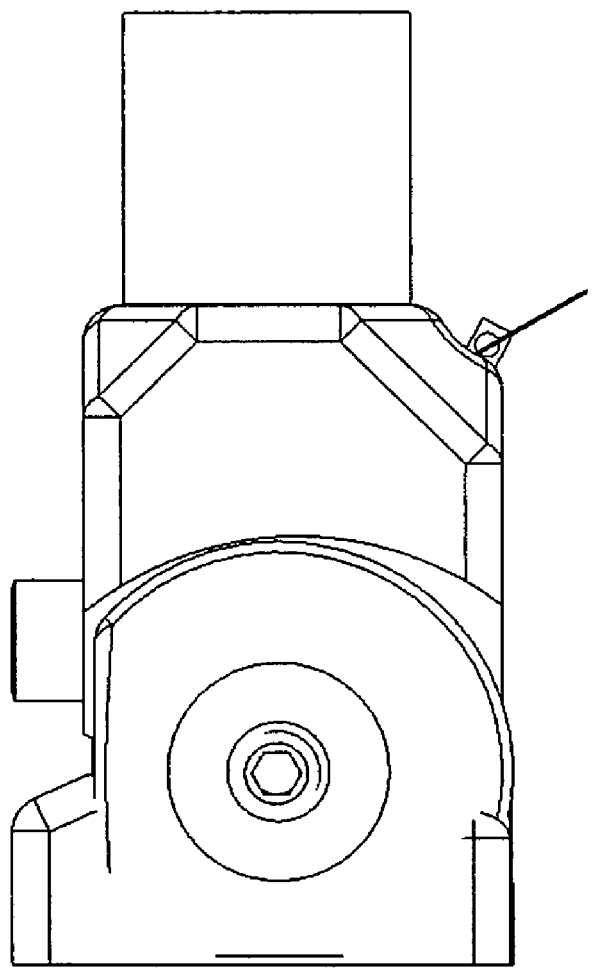
FIG. 3 Medial Side Elevation, Fully assembled Ankle Joint Prosthesis, in position suitable for walking or running.
Figure 4:
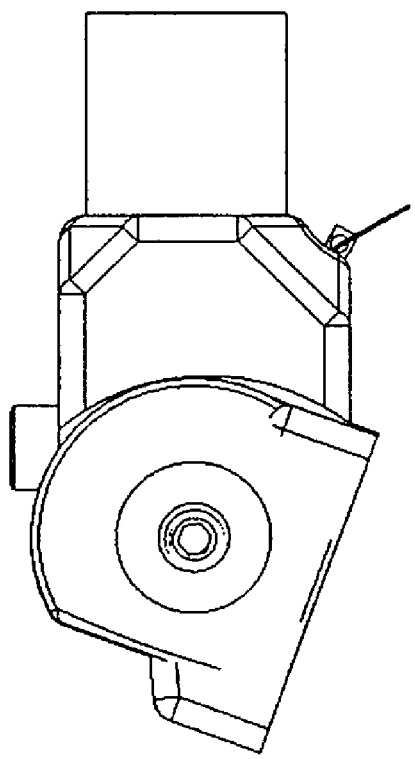
FIG. 4 Medial Side Elevation, Fully assembled Ankle Joint Prosthesis, in plantar flexion position suitable for aquatic activity.
Figure 5:
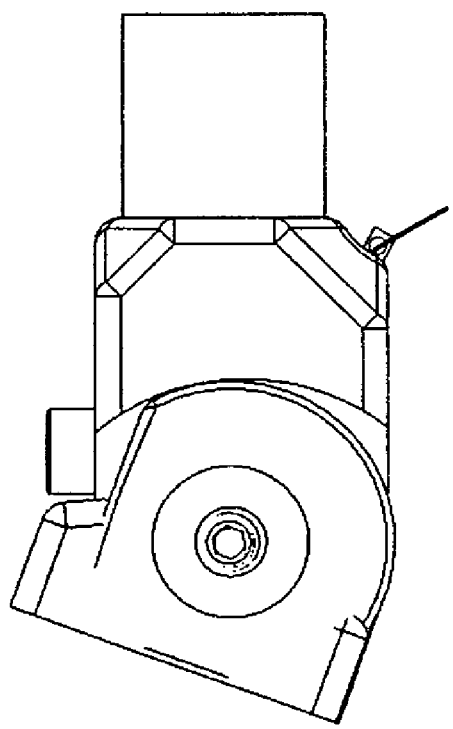
FIG. 5 Medial Side Elevation, Fully assembled Ankle Joint Prosthesis, in dorsal flexion position suitable for equestrian activity.

Referring to FIG. 2, the central core element 100 of FIG. 1 comprises an upper region 101 and lower region 102, of which the upper region 101 is precision machined into a diametrical hollow pylon designed in length and outer diameter to be compatible with 30 mm prosthetic industry tube clamp adaptor components. The lower region 102 serves as the housing for the mechanical linkage's 200, 300, and 400, and transitions to a generally shaped rectangular geometry comprising the central core anterior face 103, central core medial face 104, and central core lateral face 105. The central core medial face 104 and central core lateral face 105 are of mirror image. The central core posterior face 111 transitions over the circular counterbore 112 housing to a flat face.

Referring to FIG. 2, central core medial face 104 comprises a medial radial groove face 122 down to the central core shoulder 106, which extends perpendicular from the medial and lateral faces encircling the torsion spring housing counterbore 107 and the central axis circular bore 109. The lower section of the central core shoulder 106 spans the width of the central core element 100. The torsion spring housing counterbore 107 penetrates the central core medial face 104. Torsion spring housing counterbore 107 is a flat-bottomed counterbore. The central axis circular bore 109 penetrates the entirety of the central core element 100 body along the x-axis. The central core medial face 104 is precision machined through to form a slot 110 oriented 70 degrees from the central axis circular bore 109 y-axis plane which allows the posterior mechanical linkage 300 guide pin 301 to move; the slot 110 opening length being equal to the maximum stroke of the posterior mechanical linkage 300.

Referring to FIG. 2, circular bore 117 on central core 100 lower region 102 medial face 104 originating on the posterior radial side of the lower outer central core shoulder 106, directed through and penetrating the torsion spring housing counterbore 107 and 108 at the vortex of circular counterbore 112 centerline axis.

Referring to FIG. 2, the central core 100 of FIG. 1 comprises an upper region 101 and lower region 102. The lower region 102 of the anterior face 103 transitions to a generally flat face comprising circular bores for the anterior mechanical linkage 200 down to the central shoulder body 106 comprising the central axis mechanical linkage 400.

Referring to FIG. 2, circular counterbores 114, 115, & circular bore 116 are along the same axis centerline originating on central core 100 lower region 102 anterior face 103. The centerline of circular counterbores 114, 115, & circular bore 116 being perpendicular to the central axis midpoint. Circular bore 116 penetrates the central core posterior face, whereas circular counterbore 114 is larger than circular counterbore 115, neither penetrating beyond the central axis circular bore 109 plane.

Referring to FIG. 2, circular bore 112 on central core 100 lower region 102 anterior face 103 lower central core shoulder 106 central axis midpoint, at the 250 degree mark passing through the center of the central axis circular bore 109 of central core 100 a specific length very near, but not penetrating the top of the central core posterior face 111. Circular counterbore 112 is a flat-bottomed counterbore. Circular bore 113 passes along the same centerline as circular bore 112, however, penetrating the central core posterior face 111.

Referring to FIG. 2, the central core 100 of FIG. 1 comprises an upper region 101 and lower region 102. The lower region 102 of the posterior face 111 slopes across circular bore 113, transitions over a chamfered edge which encapsulates the posterior mechanical linkage 300 to a flat face comprising circular bore 116, the posterior stop 120, and key slot 121, down to the central core outer lower shoulder body 106.

Referring to FIG. 2, the anterior mechanical linkage 200 of FIG. 1 comprises an assembly utilizing a custom designed self-locking implanted cotter detent pin of which precision-machined characteristics are crucial to the invention. The self-locking implanted cotter detent pin of its own design is not a patentable design in this invention; however its customized application for the anterior mechanical linkage 200 is crucial. The precision machined characteristics of the anterior mechanical linkage 200 comprises a head 201 designed specifically to physically constrain the anterior mechanical linkage compression spring 203 within circular counter bore 115, and limit the linear stroke of the self-locking implanted cotter 206, which is of a critical effective measurement. Another precision machined characteristic crucial to the invention is the plunger saddle 205. The plunger saddle 205 is designed with a 45-degree slope so as to translate linear horizontal motion affecting an upward stroke of a precise measurement to the posterior mechanical linkage 300. The self-locking implanted cotter detent pin 206 is physically restrained within key slot 120 of posterior face 111 to prevent the anterior mechanical linkage 200 from retracting or rotating within circular bore 116.

Referring to FIG. 2, the posterior mechanical linkage 300 of FIG. 1 comprises an assembly of which precision machined characteristics are crucial to the invention. Precision dimensions regarding diameter, length, and bore location are crucial for the posterior mechanical linkage to fit within circular counterbore 112 and circular bore 113 and function properly in tandem with anterior mechanical linkage 200. The posterior mechanical linkage 300 comprises plunger guide pin 301, plunger body 302, plunger compression spring 303, plunger stem 304, and plunger ring 305.

Referring to FIG. 2, the central axis mechanical linkage 400 of FIG. 1 comprises a medial torsion spring 401, central axis shaft 403 lateral torsion spring 402, medial mechanical fastener 404, and lateral mechanical fastener 405. The central axis shaft 403 is not designed to be load bearing, is a precision measured length and tapped both ends to allow for mechanical fastening of the medial side element 500 and the lateral side element 600 mechanical fasteners 404 and 405 respectively.

Referring to FIG. 2, since the medial side element 500 and the lateral side element 600 of FIG. 1 are designed as mirror images of each other. For the purposes of this description, only the lateral side element 600 will be detailed.

Crucial to the medial/lateral side element designs are the radial dimensions/tolerances from the central axis plane that effect the central axis bore 610, torsion spring counterbore 611, groove profile 614, and the top rim 604 such that interference with the central core 100 is not created. The central axis circular bore 610 is used to allow connection of mechanical fastener 405 through lateral side element 600 to central axis shaft 403, thus providing the compressive force to anterior mating face 602 when applied to opposing anterior mating face 502. The torsion spring housing counterbore 611 is a flat-bottomed counterbore; is crucial due to its depth of fit in relation to the length of the central axis shaft 403, length of the central core shoulder bearing 613, and body length of the lateral torsion spring 402.

Another crucial feature of the medial/lateral side element design is the groove profile 614, which defines the groove working curve 615 and the groove inner profile 616 dimensions. The invention is applied for use during aquatic and/or equestrian activity.

Figure 6:
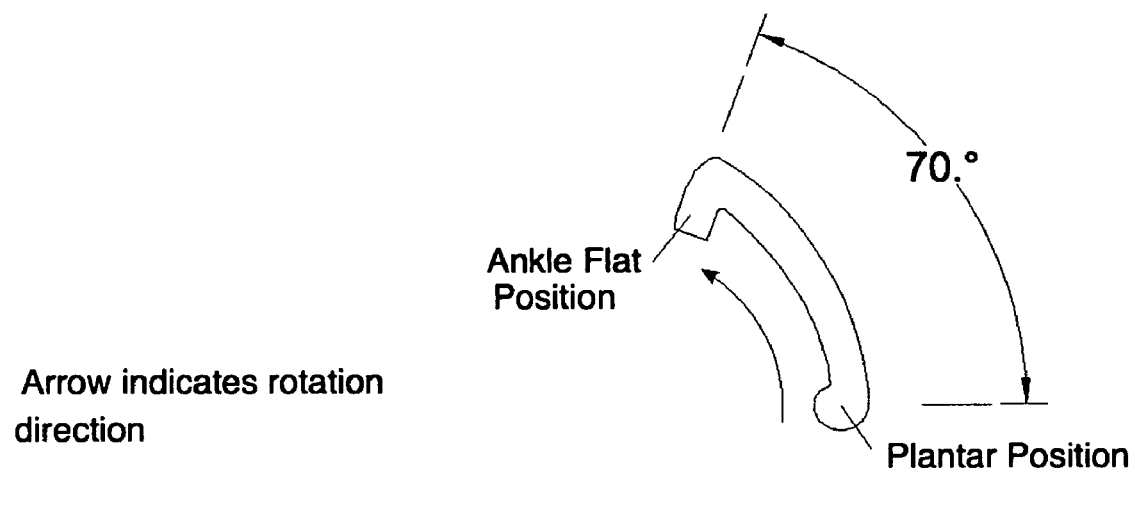
FIG. 6 Lateral Side Elevation, Aquatic Grooved Profile

Referring to FIG. 6, Aquatic grooved profile 614 is designed such that when the posterior mechanical linkage 300 is effectively moved from its least compressed static orientation, the guide pin 301 will translate via slot 110, then riding within and along the groove working curve 615 effectively allowing the lateral side element 600 to rotate until held in a dwell motion condition at a specific orientation 70 degrees plantar flexion by the combination of the plunger compression spring 303 force and the groove inner profile 616 positive mechanical constraints.

Figure 7:
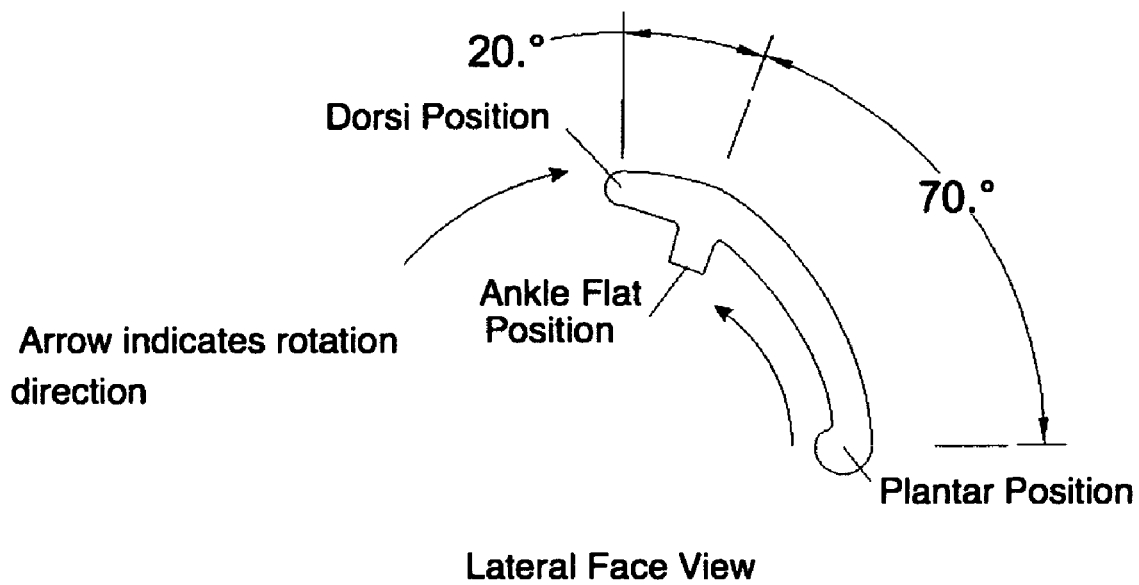
FIG. 7 Lateral Side Elevation, Surf Grooved Profile

Referring to FIG. 7, Surf grooved profile 614 is designed such that when the posterior mechanical linkage 300 is effectively moved from its least compressed static orientation, the guide pin 301 will travel a specific vertical stroke distance via slot 110, then can move along the groove working curve 615 in either radial direction effectively allowing the lateral side element 600 to rotate until held in a dwell condition at a specific orientation 70 degrees plantar flexion, or held in a dwell condition at a specific orientation 20 degrees dorsi flexion.

Figure 8:
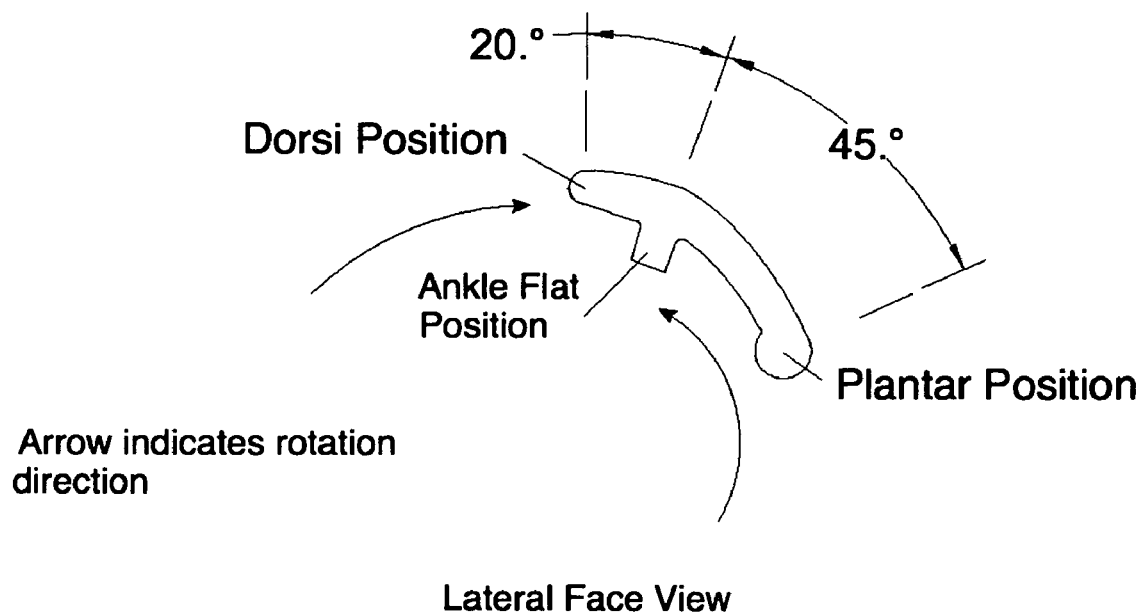
FIG. 8 Lateral Side Elevation, Equestrian Grooved Profile

Referring to FIG. 8, Equestrian grooved profile 614 is designed such that when the posterior mechanical linkage 300 is effectively moved from its least compressed static orientation, the guide pin 301 will travel a specific stroke distance constrained in slot 110, thus able to ride along the groove working curve 615 in either radial direction effectively allowing the lateral side element 600 to rotate until held in a dwell condition at a specific orientation 45 degrees plantar flexion, or held in a dwell condition at a specific orientation 20 degrees dorsi flexion.

Yet another crucial feature of the medial/lateral side element is the posterior stop 608 and the anterior stop 609, designed such that the lateral side element shall not rotate beyond specific dwell locations within the groove profile 614.

The lateral side element 600 base face 606 is designed to be compatible with prosthetic industry 4-hole adaptor components; anterior base component fastener tapped hole 619 and posterior base component tapped hole 620 are incorporated for this purpose accepting anterior base component mechanical fastener 622 and posterior base component mechanical fastener 623. Base circular bore 621 is incorporated for the removal of excess material.

Assembly of the Invention

Step 1, assembly of the posterior mechanical linkage 300 into central core element 100 is accomplished by fitting the plunger compression spring 303 over the plunger stem 304 until resting on the plunger body 302, and then inserting the assembled parts into lower outer central core shoulder body 106 circular counterbore 112 and circular bore 113. Plunger guide pin 301 is fitted through slot 110 into circular bore 306 and positioned so that plunger guide pin 301 is centered (each side length to be equal from the plunger body 302 centerline) within the plunger body 302. Plunger stem circular bore 307 must be in the same axis plane as plunger body circular bore 306. Push posterior mechanical linkage 300 assembly through circular bore 113 so that plunger stem circular bore 307 penetrates the central core posterior face 114. Insert plunger ring 305 into plunger stem circular bore 307 to complete the installation of the posterior mechanical linkage 300.

Step 2, the anterior mechanical linkage 200 is assembled by fitting the head compression spring 203 over the self locking implanted cotter detent 206 and moving the head compression spring 203 past the plunger saddle 205 until resting on the inner head shoulder 202, and then inserting the assembled parts into circular counterbores 114, 115, and into circular bore 116. Lift posterior mechanical linkage 300 by pulling plunger ring 305 in the outward & upward direction such that the anterior mechanical linkage 200 can be pushed through circular bore 116 far enough so that the self locking implanted cotter detent 206 is deployed into key slot 121, thus positively restrained.

Step 3, the central axis mechanical linkage 400 is assembled by fitting the medial torsion spring 401 upper leg and the lateral torsion spring 402 upper leg into medial torsion spring circular bores 117 and 118 respectively, located inside the torsion spring housing circular counterbores 107 and 108 respectively. The central axis shaft 403 is then fitted into either side of the central axis circular bore 109 equidistance of the central core element 100 midpoint.

Step 4, the medial side element 500 and the lateral side element 600 are assembled by press fitting the central core shoulder bearings 513 and 613 into torsion spring housing counterbore 511 and 611 respectively.

Step 5, insert the medial torsion spring 401 lower leg into medial torsion spring circular bore 518 located internal to torsion spring housing counterbore 511 on medial side element 500 inner face 503.

Step 6, fit central axis mechanical linkage mechanical fastener 404 into medial side element countersink 517 and through medial side element circular bore 510 into the threaded central axis shaft 403 and tighten such that the medial side element 500 is firmly connected with central axis shaft 403, and fitted around and onto the central core shoulder 106 such that the posterior mechanical linkage 300 guide pin 301 is fitted into the groove inner profile 516 of medial side element 500.

Step 7, insert the lateral torsion spring 402 lower leg into torsion spring leg bore 618 located internal to torsion spring housing counterbore 611 on lateral side element 600 inner face 603. Next, fit central axis mechanical linkage mechanical fastener 405 into lateral side element countersink 617 and through central axis circular bore 610 into the threaded central axis shaft 403 and tighten such that the lateral side element 600 is firmly connected with central axis shaft 403, and fitted around and onto the central core shoulder 106 such that the posterior mechanical linkage 300 guide pin 301 is fitted into the groove inner profile 616 of lateral side element 600, and medial side element 500 anterior mating face 502 is aligned and flat against lateral side element 600 anterior mating face 602.

Step 8, fit lateral side element mechanical fastener 622 and 623 through a prosthetic industry 4-hole adaptor component 725 base into anterior base component fastener tapped hole 619 and posterior base component tapped hole 620 respectively, and tighten per component manufacturer torque value instructions such that the 4-hole adaptor component is firmly connected with the lateral side element 600. Repeat step 8 for the medial side element mechanical fasteners 522 and 523.

Step 9, affix a 30 mm prosthetic industry tube clamp adaptor component 750 onto the central core 100 upper region 101 and tighten per component manufacturer torque value instructions.

Figure 9:
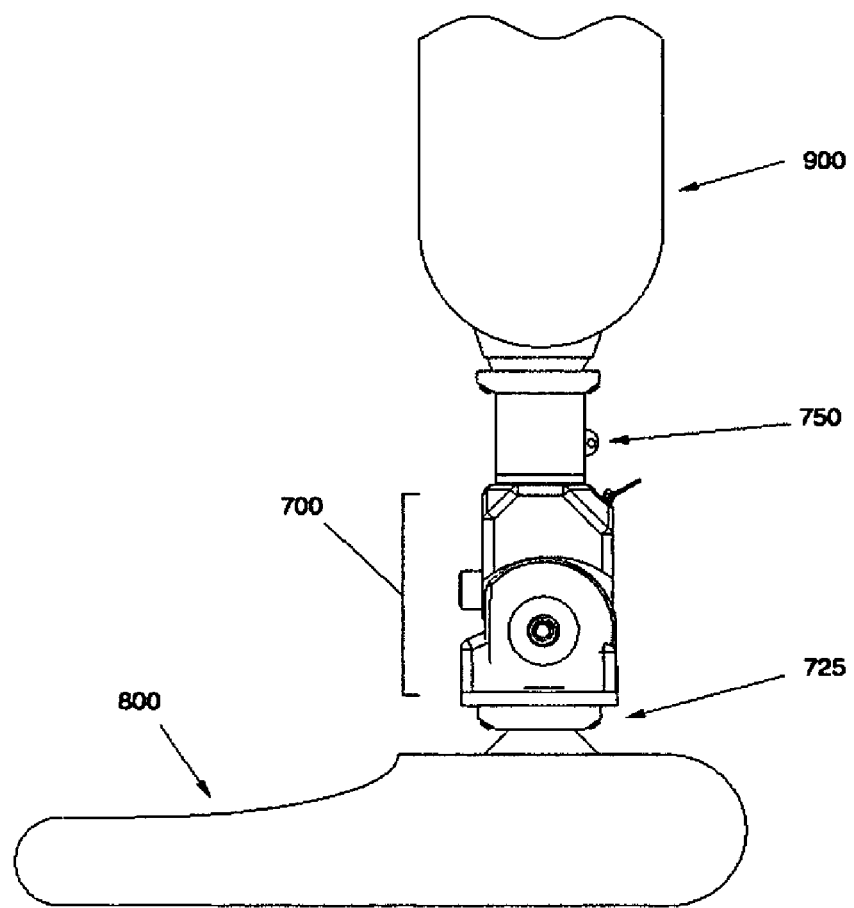
FIG. 9 Fully assembled Ankle Joint Prosthesis attached to artificial leg and artificial foot.

Step 10, Referring to FIG. 9, Affix the completely assembled ankle joint prosthesis 700 to an artificial foot 800 and an artificial leg 900.

Operation of the Invention

Referring to FIG. 9, Position the ankle joint prosthesis 700 such that the artificial foot 800 is in the "foot flat" o degree orientation for terrestrial bipedal locomotion use. The key feature of the invention is that the ankle joint prosthesis 700 can have its orientation repositioned without the user having to stop activity and manually establish the desired orientation and lock into position.

For use in an aquatic sports activity, such as; swimming, scuba diving, wade fishing, or triathlon, use the aquatic grooved profile. Walk, run, or jump into the water and depress the anterior mechanical linkage 200, thus forcing the posterior mechanical linkage 300 to stroke and allowing the medial and lateral side elements 500 and 600 respectively to rotate via torsion force from central axis mechanical linkage 400, thus positioning the artificial foot 800 into a 70 degree plantar flexion orientation relative to the artificial leg 900.

Depress the anterior mechanical linkage 200 by kicking head 201 with the posterior side of the users' heel from the opposite leg to accomplish engagement for a "hands free" interface, otherwise one can pull the posterior mechanical linkage 300 plunger ring 305 to accomplish the same result.

Transition from an aquatic environment to terra firma is accomplished by simply applying a force through artificial leg 900 to the bottom forefoot of the artificial foot 800, thus causing a reverse rotation of the ankle joint prosthesis 700 back to the "foot flat" o degree orientation for terrestrial bipedal locomotion use; i.e. no manual manipulation by hand of the ankle joint prosthesis 700 is required.

For use in an equestrian sports activity, such as; horseback riding, use the equestrian grooved profile. This specific groove profile is designed for use for walking and while riding in a saddle atop a horse. Use of the anterior mechanical linkage 200 is not utilized; however the posterior mechanical linkage 300 is manually pulled upward allowing the medial and lateral side elements 500 and 600 respectively to ride along the working curve of the grooved profile.

By pulling the posterior mechanical linkage 300 plunger ring 305 upward/outward and applying a force through artificial leg 900 to the bottom forefoot of the artificial foot 800, artificial foot 800 will rotate to a 20 degree dorsi-flexion "heel down" orientation.

Transition while in the saddle seat of the ankle joint prosthesis 700 such that the artificial foot returns to the "foot flat" o degree orientation is accomplished by simply lifting the force from the artificial foot 800 forefoot, thus removing force through the artificial leg 900, causing a rotation of the ankle joint prosthesis 700 via torsion force from central axis mechanical linkage 400 back to the "foot flat" o degree orientation without having to manually rotate and fix the ankle into the desired orientation by hand, which enables the equestrian enthusiast proper weight distribution providing improved balance and stability.

Transition from the saddle seat to terra firma is accomplished by relieving any pressure to the artificial foot 800 and pulling the posterior mechanical linkage 300 plunger ring 305 upward/outward, thus allowing the medial and lateral side elements 500 and 600 respectively to rotate via torsion force from central axis mechanical linkage 400, thus positioning the artificial foot 800 into a 45 degree plantar flexion orientation relative to the artificial leg 900 so that the artificial foot 800 can easily be extracted from the saddle stirrup.

For use in an aquatic sports activity, such as surfing, use the surf grooved profile. Walk or jump into the water and depress the anterior mechanical linkage 200, thus forcing the posterior mechanical linkage 300 to stroke and allowing the medial and lateral side elements 500 and 600 respectively to rotate via torsion force from central axis mechanical linkage 400, thus positioning the artificial foot 800 into a 80 degree plantar flexion orientation relative to the artificial leg 900 for swimming or in the kneeling position on the surf board.

Depress the anterior mechanical linkage 200 by kicking head 201 with the posterior side of the users heel of the opposite leg to accomplish engagement for a "hands free" operational interface, otherwise pull the posterior mechanical linkage 300 plunger ring 305 to accomplish the same result.

Stand on the surfboard and apply a force through artificial leg 900 to the bottom forefoot of the artificial foot 800, thus causing a reverse rotation of the ankle joint prosthesis 700 back to the "foot flat" o degree orientation. To stabilize your stance and obtain a squatting forward position, simply pull the posterior mechanical linkage 300 plunger ring 305 upward/outward and apply a force through artificial leg 900 to the bottom forefoot of the artificial foot 800, artificial foot 800 will rotate to a 20 degree dorsi-flexion orientation.

Transition of the ankle joint prosthesis 700 such that the artificial foot returns to the "foot flat" o degree orientation is accomplished by simply lifting the artificial foot 800 forefoot, thus removing force through the artificial leg 900, causing a rotation of the ankle joint prosthesis 700 via torsion force from central axis mechanical linkage 400 back to the "foot flat" o degree orientation without having to manually rotate and fix the ankle into the desired orientation by hand.

Transition from an aquatic environment to terra firma if in the 80 degree plantar flexion orientation is accomplished by simply applying a force through artificial leg 900 to the bottom forefoot of the artificial foot 800, thus causing a reverse rotation of the ankle joint prosthesis 700 back to the "foot flat" o degree orientation for terrestrial bipedal locomotion use; i.e. no manual manipulation by hand of the ankle joint prosthesis 700 is required.

I claim:

1. A prosthetic device, an ankle joint prosthesis for attachment to an artificial leg with an artificial foot, consisting of:
    a central core element;
    an anterior mechanical linkage;
    a posterior mechanical linkage;
    a central axis mechanical linkage;
    a medial side element;
    a lateral side element;
    wherein said central core element is defined as a waterproof and corrosion resistant precision machined part consisting of an upper region and a lower region;
    wherein said upper region consists of a diametrical hollow pylon designed in length and outer diameter to be compatible with 30 mm prosthetic industry tube clamp adaptor components used in conjunction for attachment to the artificial leg;
    wherein said lower region consists of a geometric transition from a diametric to rectangular element including an anterior face, a medial face, a lateral face, a posterior face, and a diametric shoulder; all of which embody the anterior, posterior, and central core mechanical linkages, and provides the support in which the medial and lateral side elements relatively rotate;
    wherein said anterior mechanical linkage is defined as an assembly utilized as a positive mechanical constraint to the posterior mechanical linkage, which translates linear horizontal motion affecting an upward stroke of a compression spring constrained posterior mechanical linkage in an angular plane 70 degrees from normal to an axis of rotation of the central axis mechanical linkage;
    wherein said posterior mechanical linkage is defined as an assembly utilized as a compression spring constraint applying pressure on a plunger body and a plunger guide pin thus maintaining constant positive mechanical contact with the anterior mechanical linkage and a medial and lateral side element groove profile respectively, which act as positive mechanical constraints throughout the posterior mechanical linkage motion cycle;
    wherein said central axis mechanical linkage is defined as an assembly utilized as a torsion spring constraint applying constant pressure on the plunger guide pin thus maintaining constant positive mechanical contact with the medial and lateral side element groove profile whereby affecting a torsion force onto the medial and lateral side elements causing said side elements to rotate;
    wherein said medial side element is defined as a waterproof and corrosion resistant precision machined part consisting of integral groove profile and physical connection to the central axis mechanical linkage whereby coupled onto the central core element effecting a rotation relative to the central core element; coupled side element pair base is compatible with prosthetic industry adaptor components and used in conjunction for attachment to an artificial foot;
    wherein said lateral side element is defined as a waterproof and corrosion resistant precision machined part consisting of an integral groove profile and a physical connection to the central axis mechanical linkage whereby coupled onto the central core element effecting a rotation relative to the central core element; coupled side element pair base is compatible with prosthetic industry adaptor components and used in conjunction for attachment to an artificial foot.

2. A prosthetic device, an ankle joint prosthesis for attachment to an artificial leg with an artificial foot comprised of an interchangeable lateral and medial side element pair, each side element pair having a specific grooved profile designed for achieving a specific foot orientation for use in aquatic or equestrian activity;
    wherein said medial side element is defined as a waterproof and corrosion resistant precision machined part consisting of an integral groove profile and a physical mechanical connection to a central axis mechanical linkage whereby coupled onto a central core element effecting a rotation motion relative to the central core element; coupled side element pair base is compatible with prosthetic industry adaptor components and used in conjunction for attachment to the artificial foot;
    wherein said lateral side element is defined as a waterproof and corrosion resistant precision machined part consisting of an integral groove profile and a physical mechanical connection to the central axis mechanical linkage whereby coupled onto the central core element effecting a rotation motion relative to the central core element; coupled side element pair base is compatible with prosthetic industry adaptor components and used in conjunction for attachment to the artificial foot;
    wherein said central axis mechanical linkage is defined as an assembly utilized as a torsion spring constraint applying constant pressure on a plunger guide pin thus maintaining constant positive mechanical contact with the medial and lateral side element groove profile whereby affecting a torsion force onto the medial and lateral side elements causing said side elements to rotate;
    wherein said interchangeable is defined as capable of being used in place of each other; one pair of side elements for aquatic activity and another pair of side elements for equestrian riding activity;
    wherein said specific grooved profile is defined as a groove cut/milled into a side element inner face a specific dimension (height and depth) along a specific working curve; a curve path designed for aquatic activity orientation, and a curve path designed for equestrian riding activity orientation.

3. An ankle joint prosthesis of claim 1, having mechanical linkage engagement positions located in the anterior face and posterior face of the central core element; whereby affecting translation of the anterior mechanical linkage and the posterior mechanical linkage, whereby affecting a rotation motion of said medial side element and lateral side element by the central axis mechanical linkage;
    wherein said anterior face is defined as the front area of the central core element flat face comprising circular bores for housing the anterior mechanical linkage;

wherein the posterior face is defined as the rear area of the central core element comprising circular bores for housing the anterior mechanical linkage and the posterior mechanical linkage;

wherein torsion load is defined as the twisting effect caused by the torque produced by the central axis mechanical linkage.

4. An ankle joint prosthesis of claim 1 or claim 2 which comprises the utilization of a torsion load produced by the central axis mechanical linkage to affect said medial side element and lateral side element orientation as defined by a grooved profile and a working curve;

wherein said torsion load is defined as the twisting effect caused by the torque produced by torsion springs within the central axis mechanical linkage.

* * * * *